United States Patent
Ujihara et al.

(10) Patent No.: US 6,770,618 B2
(45) Date of Patent: Aug. 3, 2004

(54) (1S,6R)-2,2,6-TRIMETHYLCYCLOHEXYL METHYL KETONE AND/OR (1R,6S)-2,2,6-TRIMETHYLCYCLOHEXYL METHYL KETONE, PROCESS FOR PRODUCING THE SAME, AND PERFUME COMPOSITION CONTAINING THE SAME

(75) Inventors: Hideo Ujihara, Yokohama (JP); Shinya Watanabe, Hiratsuka (JP); Takeshi Yamamoto, Kawasaki (JP); Toshimitsu Hagiwara, Yokohama (JP)

(73) Assignee: Takasago International Corp., Tokyo (JP)

( * ) Notice: Subject to any disclaimer, the term of this patent is extended or adjusted under 35 U.S.C. 154(b) by 315 days.

(21) Appl. No.: 09/876,883

(22) Filed: Jun. 7, 2001

(65) Prior Publication Data

US 2002/0042356 A1 Apr. 11, 2002

(30) Foreign Application Priority Data

Jun. 7, 2000 (JP) ........................................ 2000-170822

(51) Int. Cl.$^7$ .............................. A61K 7/46; C07C 49/11
(52) U.S. Cl. ................................. 512/27; 512/8; 512/22; 512/23; 512/24; 512/25; 512/26; 568/303; 568/338; 568/341; 568/365; 568/366; 568/376; 568/377; 585/20; 585/23; 585/350; 585/365
(58) Field of Search .............................. 512/8, 25, 22, 512/23, 24, 26, 27; 568/303, 338, 341, 365, 366, 376, 377; 585/20, 23, 350, 365

(56) References Cited

U.S. PATENT DOCUMENTS

| 4,109,022 A | | 8/1978 | De Haan et al. | |
| 4,136,066 A | * | 1/1979 | De Haan et al. | ............... 512/24 |

FOREIGN PATENT DOCUMENTS

| FR | 676393 | * 10/1995 |
| JP | 4330033 | 11/1992 |

OTHER PUBLICATIONS

J. Org, Chem., "Reduction of Organic Compounds with Solutions of Ytterbium in Liquid Ammonia", 43, pp. 4555–4558, (1978).

International Congress of Essential Oils, "Chemical Transformation of Citronellal", 7, pp. 253–256 (1979).

Revue Roumaine de Chimie, "Cyclisation Radicalaires D'Aldehydes Ethyleniques", 26, pp. 275–282, (1981).

Helv. Chim. Acta, "263, Absolute Konfiguration der enantiomeren . . . ", 56, pp. 2548–2563 (1973).

* cited by examiner

Primary Examiner—Jill Warden
Assistant Examiner—Monique T. Cole
(74) Attorney, Agent, or Firm—Darby & Darby

(57) ABSTRACT

Trans-2,2,6-trimethylcyclohexyl methyl ketone, including (1S,6R)-2,2,6-trimethylcyclohexyl methyl ketone represented by the formula (1a):

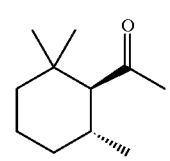

(1a)

(1S, 6R)- and (1R,6S)-2,2,6-trimethylcyclohexyl methyl ketone represented by the formula (1b):

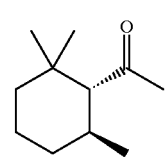

(1b)

(1R, 6S)- are useful components in a perfume composition. A process for producing the same is also described. A unique eucalyptus, mint-like and white floral perfume material is provided using the ketone compounds disclosed in the present invention. The process of the present invention produces the optically active ketone compounds having optical purity up to at least 98.0 % e.e.

8 Claims, No Drawings

(1S,6R)-2,2,6-TRIMETHYLCYCLOHEXYL METHYL KETONE AND/OR (1R,6S)-2,2,6-TRIMETHYLCYCLOHEXYL METHYL KETONE, PROCESS FOR PRODUCING THE SAME, AND PERFUME COMPOSITION CONTAINING THE SAME

BACKGROUND OF THE INVENTION

1. Field of the Invention

The present invention relates to a perfume or perfume intermediate used in fragrant cosmetics, and more particularly, to the trans form of (1S,6R)-2,2,6-trimethylcyclohexyl methyl ketone and/or (1R,6S)-2,2,6-trimethylcyclohexyl methyl ketone, a process for producing the same and a perfume composition containing the same.

2. Description of the Related Art

Although the reports given below have been made with respect to 2,2,6-trimethylcyclohexyl methyl ketone (1), none of these reports relate to its fragrance. As an example of synthesis of the racemic form, 2,2,6-trimethylcyclohexyl methyl ketone (1), James D. White et al. (J. Org. Chem. (1978), 43(23), 4555–4556) synthesized 2,2,6-trimethylcyclohexyl methyl ketone (1) by hydrogenating 2,6,6-trimethyl-1-cyclohexenyl methyl ketone (3) with a ytterbium catalyst in liquid ammonia as indicated by the formula below at yield of 81% (the ratio between the cis and trans forms is unknown).

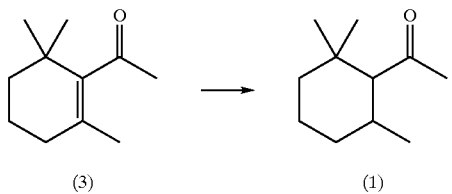

In addition, as indicated by the formula below, R. A. Barnes et al. (Int. Cong. Essen. Oils, 7th (1979), Meeting Date 1977, Volume 7, 253–256, Publisher, Japan Flavor Fragrance Manufacturers' Asso., Tokyo, Japan) describes a method characterized by obtaining homocitronellol (5) by reacting citronellal (4) with methyl magnesium chloride followed by cyclization with acid, while yield and the ratio between the cis and trans forms are unknown.

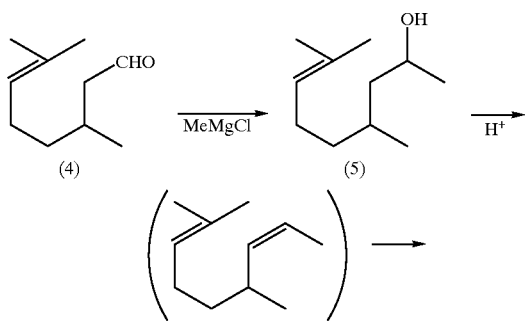

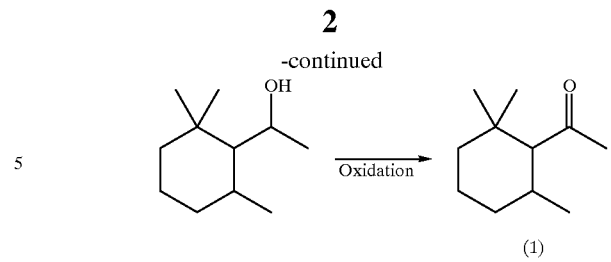

As indicated by the formula below, M. Chatzopoulos et al. (Revue Roumaine de Chimie, 26, 2, 275–282 (1981)) synthesized 2,2,6-trimethylcyclohexyl methyl ketone (1) at a yield of 30% using 4,8-dimethylnonan-2-one (6) and a radical initiator (D.T.B.P.). The ratio between the cis and trans forms is unknown in this case as well.

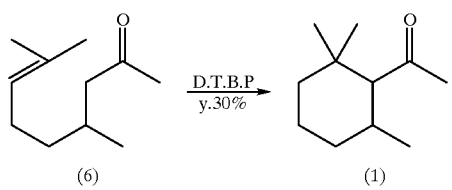

In addition, as indicated by the following formula Douwe R. De Haan et al. (Japanese Patent Publication No. 57-36252, DE 2353578) synthesized cis-2,2,6-trimethylcyclohexyl methyl ketone (racemic cis-(1)) by hydrogenation of 2,6,6-trimethyl-3-cyclohexenyl methyl ketone (9) obtained in a Diels-Alder reaction between 1,3-pentadiene (7) and mesityl oxide (8), and synthesized trans-2,2,6-trimethylcyclohexyl methyl ketone (racemic trans-(1)) by treating the racemic cis-(1) with polyphosphoric acid.

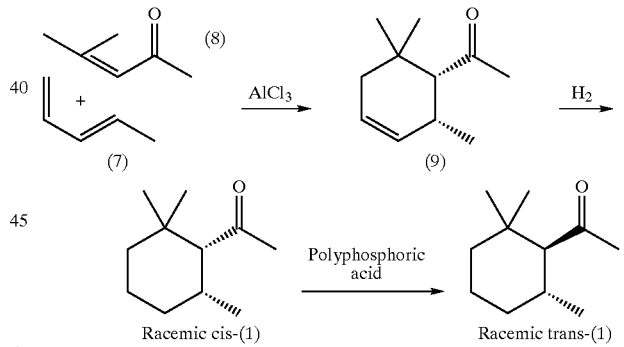

With respect to optically active substances, Richard Buchecker et al. (Helv. Chim. Acta (1973), 56(7), 2548–2563) reported the cis form indicated by the following formula, namely the (1R,6R) form (formula (1c)) and/or the (1S,6S) form (formula (1d)).

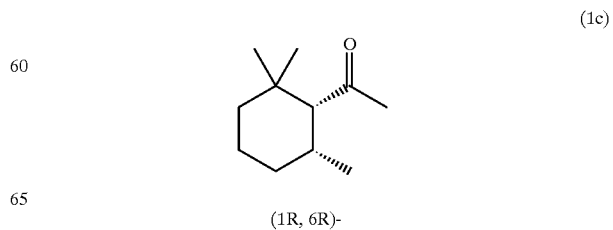

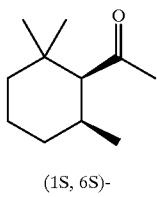

(1S, 6S)-

However, they derived and synthesized these compounds from the viewpoint of research on the absolute structure of α-cyclogeranic acid, α-cyclogeranial, α-ionone, γ-ionone, etc., and there is no description of their fragrance. In addition, there is no mention of the trans forms that are the compounds of the present invention, namely the (1S,6R) form represented by the formula (1a) and/or the (1R,6S) form represented by the formula (1b), and these were not known compounds.

On the other hand, the fruity floral perfume, 1-(2,2,6-trimethylcyclohexyl)-2-buten-1-one (10) is a known example of a perfume that is derived from 2,2,6-trimethylcyclohexyl methyl ketone (1). With respect to the racemic forms of this compound, according to the previously mentioned Douwe R. De Haan et al. (Japanese Patent Publication No. 57-36252, DE 2353578), the cis and trans forms of 1-(2,2,6-trimethylcyclohexyl)-2-buten-1-one (Racemic cis-(10)) and (Racemic trans-(10)) are produced by the method indicated by the following formulas:

(wherein wave lines indicate the cis or trans form).

In addition, with respect to the optically active 1-(2,2,6-trimethylcyclohexyl)-2-buten-1-one (the (1S,6R) form is referred to as (10a), while the (1R,6S) form is referred to as (10b)), the inventors of the present invention synthesized this optically active compound using the method indicated below (in accordance with Japanese Patent No. 2748184) using optically active dihydrocyclocitral ((1S,6R) form (formula (11a) and/or (1R,6S) form (formula (11b)) as the starting material, and found there to be a considerable difference in fragrance between the enantiomers, and that both exhibit superior fragrance characteristics that are different from the racemic forms.

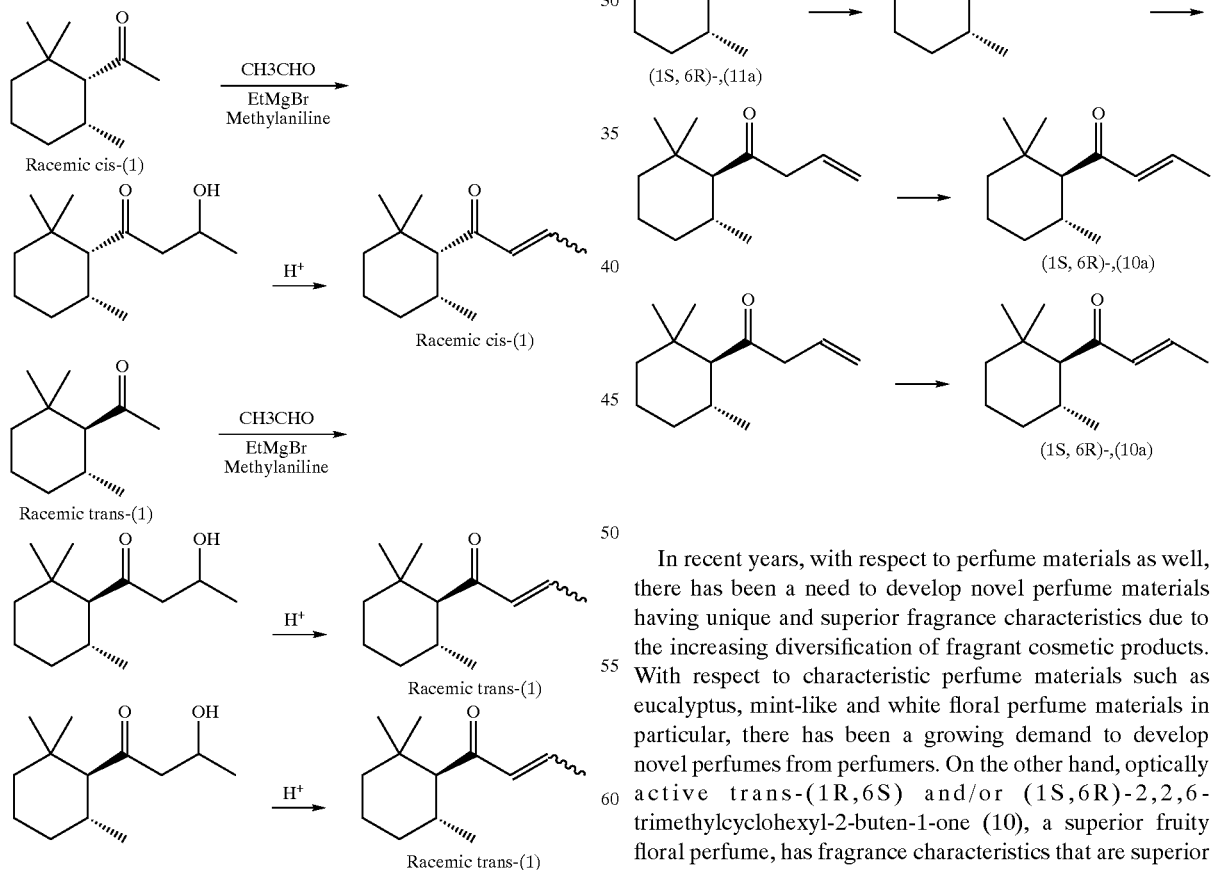

In recent years, with respect to perfume materials as well, there has been a need to develop novel perfume materials having unique and superior fragrance characteristics due to the increasing diversification of fragrant cosmetic products. With respect to characteristic perfume materials such as eucalyptus, mint-like and white floral perfume materials in particular, there has been a growing demand to develop novel perfumes from perfumers. On the other hand, optically active trans-(1R,6S) and/or (1S,6R)-2,2,6-trimethylcyclohexyl-2-buten-1-one (10), a superior fruity floral perfume, has fragrance characteristics that are superior to its racemic forms, and is desired to be used in high concentrations in terms of formulation. However, as a result of its high price placing limitations on its use, there has been a desire to develop a less expensive production method.

OBJECTS AND SUMMARY OF THE INVENTION

A first object of the present invention is to provide a unique and superior eucalyptus, mint-like or white floral novel perfume material for which there is a high demand for development from perfumers, along with a method for economically producing such a perfume material.

A second object of the present invention is to enable more economical production of optically active trans-(1S,6R)- and/or (1R,6S)-2,2,6-trimethylcyclohexyl-2-buten-1-one (10).

As a result of conducting earnest studies in consideration of the above circumstances, the inventors of the present invention found that the following novel trans forms of (1R,6S)- and/or (1S,6R)-2,2,6-trimethylcyclohexyl methyl ketone have unique and superior eucalyptus, mint-like and white floral-like fragrances different from their racemic forms, and that they are extremely useful as a novel perfume material. In addition, with respect to a production method, the inventors of the present invention also developed an inexpensive, novel production method, and accomplished the present invention. It should be noted that, as a result of allowing these novel optically active trans-2,2,6-methylcyclohexyl methyl ketones ((1S,6R) form (1a) and/or (1R,6S) form (1b)) to be produced with a novel inexpensive method, by using these as starting materials, it has become possible to provide optically active trans-1-(2,2,6-trimethylcyclohexyl)-2-buten-1-one ((1S,6R) form (10a) and/or (1R,6S) form (10b)) having superior fragrance characteristics as compared with their racemic forms less expensively than by the methods of the prior art.

Namely, the present invention provides trans-2,2,6-trimethylcyclohexyl methyl ketone, which is (1S,6R)-2,2,6-trimethylcyclohexyl methyl ketone represented by the formula (1a):

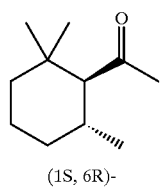

(1a)

(1S, 6R)- and/or (1R,6S)-2,2,6-trimethylcyclohexyl methyl ketone represented by the formula (1b):

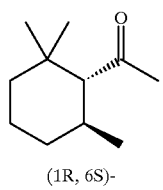

(1b)

(1R, 6S)- as well as a process for producing trans-2,2,6-trimethylcyclohexyl methyl ketone represented by the above formula (1a) and/or the formula (1b), the process comprising cyclizing a novel optically active enol acetate represented by the formula (2a):

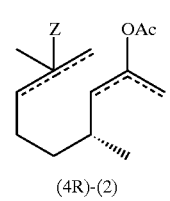

(2a)

(4R)-(2)

and/or the formula (2b):

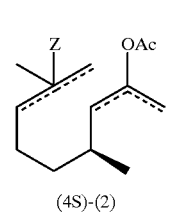

(2b)

(4S)-(2)

(wherein Ac represents an acetyl group; double lines composed of solid lines and broken lines represent a double bond or a single bond; Z represents a hydroxyl group or methoxy group in the case the double lines represent a single bond; and Z is not present in the case the double lines represent a double bond) in the presence of an acid catalyst.

Other aspects and advantages of the invention will become apparent from the following description illustrating by way of example the principles of the invention.

DETAILED DESCRIPTION OF THE INVENTION

In the following, the present invention will be explained in more detail.

In the present invention, a novel production method indicated by the following formulas was developed with respect to a production process of a novel trans-(1S,6R)- and/or (1R,6S)-2,2,6-trimethylcyclohexyl methyl ketone (1).

Reaction scheme A

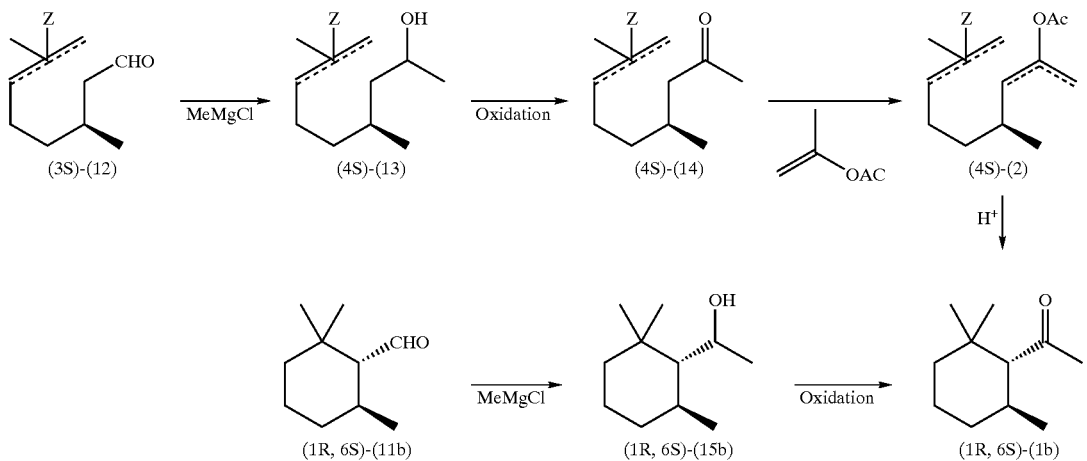

Specifically, an explanation is first provided of the production method of trans-(1R,6S)-2,2,6-trimethylcyclohexyl methyl ketone (1b).

The secondary alcohol form of the formula (13) is synthesized by using as the starting materials the (3S) form of methoxycitronellal (12, Z represents a methoxy group), 7-hydroxycitronellal (12, Z represents a hydroxyl group), citronellal (12, one of the broken lines represents a double bond) and 3,7-dimethyl-7-octene-1-al, etc. and reacting with methylmagnesium chloride. In this reaction 0.95 to 2.5 equivalents, and preferably 1.05 to 1.7 equivalents, of methylmagnesium chloride is used relative to 1 equivalent each of the starting material substances in the form of the (3S) form of methoxycitronellal (12, Z represents a methoxy group), 7-hydroxycitronellal (12, Z represents a hydroxyl group) and citronellal (12), and the solvent is selected from tetrahydrofuran (THF), dimethyl ether and diethyl ether, and the reaction temperature is from −25° C. to 60° C., and preferably from −5° C. to 25° C.

After distilling off the solvent from the resulting ether solution, oxidation is performed by adding a solvent such as alcohol and an oxidizing agent to obtain a ketone form (14). Examples of oxidizing agents that can be used include typical oxidizing agents such as a dehydrogenation catalyst like a copper-chromium catalyst or Jones reagent. The ratio of alcohol and oxidizing agent is 1.0 to 4.0 equivalents, and preferably 1.1 to 3.0 equivalents, of oxidizing agent relative to 1 equivalent of alcohol. In the case of using a dehydrogenation catalyst, the reaction temperature is from 170° C. to 250° C. in the absence of solvent or using a glycol such as polyethylene glycol as a solvent. After either filtering out the oxidizing agent from the resulting ketone ((4S)-(14)) reaction mixture, distilling out and additionally purifying or leaving it in the mixture and adding a solvent as necessary, the mixture is reacted with isopropenyl acetate in the presence of acid catalyst to obtain a novel enol acetate form ((4S)-(2)). The amount of isopropenyl acetate is 1.0 to 4.0 equivalents, and the amount of acid catalyst is 0.1 to 1 equivalent relative to 1 equivalent of ketone ((4S)-(14)).

Moreover, the desired compound (1R,6S)-(1b) can be obtained by cyclizing the resulting enol acetate form ((4S)-(2)) with an acid catalyst.

The novel optically active enol acetate form ((4S)-(2)), which serves as the key substance of the present invention, is composed of the three types of double bond isomers represented by the formulas below ((4S)-(2-1), (4S)-(2-2) and (4S)-(2-3)). The desired compound (1R,6S)-(1b) can be obtained at high yield by reacting the double bond isomers with an acid catalyst such as protonic acid in the form of a mixture as such without isolating them.

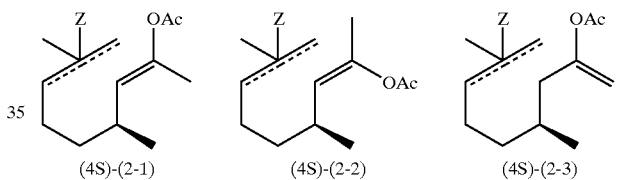

While the amount of protonic acid used varies depending on the type of acid, it is usually used within the range of 0.1 to 5 equivalents. In addition, the absence of a solvent does not present any problems, but hydrocarbons such as toluene and n-heptane or ethers such as THF can be used. The amount of protonic acid used varies depending on the type of acid, but it is usually used within the range of 0.1 to 5 equivalents relative to 1 equivalent of the enol acetate form ((4S)-(2)). The reaction temperature is from 0° C. to 220° C., and preferably from 25° C. to 160° C.

Examples of protonic acids used here include hydrochloric acid, sulfuric acid, phosphoric acid, polyphosphoric acid, para-toluenesulfonic acid, naphthalene sulfonic acid, Amberlyst-15, sulfuric acid-carrying activated clay and Nafion H. Moreover, zeolite, silica alumina, silica gel and so forth can be used as a catalyst.

Next, a novel trans-(1S,6R)-2,2,6-trimethylcyclohexyl methyl ketone (1a), which is an enantiomer of the above optically active trans-(1R,6S)-2,2,6-trimethylcyclohexyl methyl ketone (1b), can be synthesized as shown below by cyclizing the enol acetate form ((4R)-(2)), which can be synthesized using ((3R)-(12)) as the starting material, in the same manner as ((4S)-(2)).

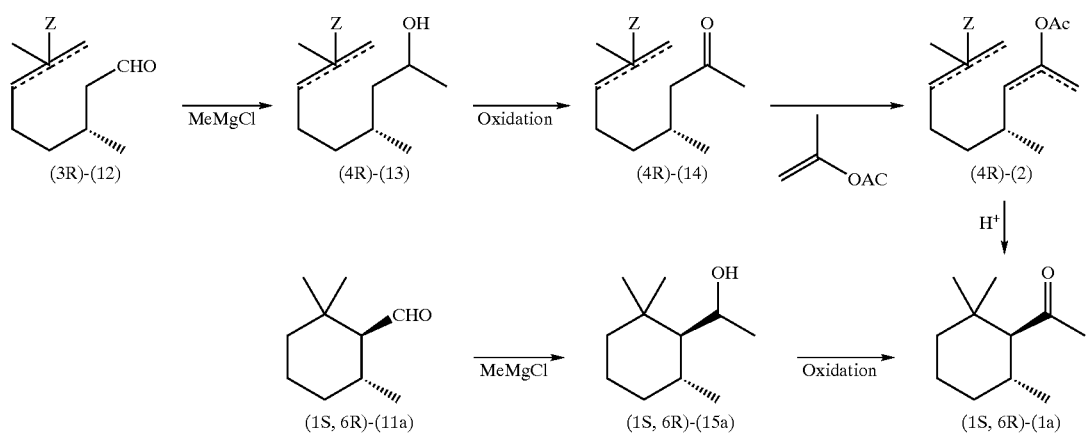

Reaction scheme B

The optical purity of the novel optically active trans-(1R, 6S)- and/or (1S,6R)-2,2,6-trimethylcyclohexyl methyl ketone ((1b),(1a)) synthesized in this manner is a reflection of the optical purity of the starting materials since there is no racemization in the reaction step of the present invention. Namely, in the case of using as starting material the (3S)- or (3R)-citronellal manufactured by Takasago International Corporation (both forms having optical purity of 98% e.e. (e.e.: enantiomer excess)), the optical purities of the (1R,6S) form and (1S,6R) form, which are compounds of the present invention, are both extremely high at 98% e.e., and as shown in Table 1, trans-(1R,6S) form compound (1b) and (1S,6R) form compound (1a) are obtained having fragrance characteristics with excellent tasteful appeal.

TABLE 1

| Compound | Absolute configuration | % e.e. | Fragrance |
|---|---|---|---|
| (structure) | (1S, 6R)-(1) | 98.0 | Pleasant mint-like, camphor-like fragrance that is extremely sharp, strongly dispersing and characteristic |
| (structure) | (1S, 6R)-(1) | 98.0 | Characteristic marine, ozone and white floral fragrance in which the mint-like and camphor-like fragrance is weaker resulting in a softer aroma overall |

Note:
The evaluation samples are those prepared in Examples 1 and 2 described later.

It should be noted that trans form (1) can be prepared having a desired optical purity by arbitrarily mixing (1a) and (1b) having optical purity of 98% e.e. With respect to the relationship between the optical purity and fragrance characteristics of (1a) and/or (1b), although fragrance characteristics are improved the higher the optical purity, if the optical purity is less than 75% e.e., it becomes difficult to demonstrate the characteristics of the optically active form, thereby decreasing value as a perfume and resulting in fragrance characteristics that are similar to the racemic form (comparative values are shown in Examples described later).

In addition to the method of the present invention, (1a) and/or (1b) can also be produced by reacting (1S,6R)- or (1R,6S)-dihydrocyclocitral ((11a) or (11b)) with methyl magnesium chloride to form (1S,6R)- or 1-(1R,6S)-2,2,6-trimethylcyclohexyl)-ethan-1-ol ((15a) or (15b)) followed by oxidizing with a copper-chromium catalyst and so forth (see Reaction scheme A described above).

Numerous reports have recently been published relating to the fragrances of enantiomers of optically active perfume compounds due to the progress made in the synthesis techniques and analytical methods employed for optically active compounds (e.g., Yamamoto, Perfume, Vol 184, pp. 57–72, 1997 and T. Yamamoto, Current Topics in Flavors and Fragrances, ed. by Karl A. D. Swift (1999), pp. 33–58).

Among these, there are cases in which fragrance characteristics between enantiomers are occasionally so extremely different that they appear to be from compounds having different structures, while in other cases, the differences can hardly be recognized. In addition, even in cases in which fragrances are quite different, there are examples of both enantiomers having fragrances superior to any of the racemic forms, examples of one of the enantiomers having superior fragrance characteristics while the other demonstrates a rather foul odor, and examples of one of the enantiomers being essentially odorless. In this manner, despite numerous facts having already been revealed, predicting differences in fragrance characteristics between enantiomers of a particular novel optically active compound based on its chemical structure is virtually impossible even for an expert, and can only be determined by actually synthesizing the compound and confirming its fragrance.

What is surprising in the case of the compounds of the present invention is that a significant difference was observed between enantiomers, and both enantiomers were determined to be excellent perfume materials. Namely, in the case of the trans-(1S,6R) form (1a), although it was determined to demonstrate a pleasant mint-like, camphor-like fragrance that is extremely sharp, strongly dispersing and characteristic, and was found to be useful in formulated perfumes in which eucalyptus oil used in the past has been modulated, the trans-(1R,6S) form (1b) emits a characteristic marine, ozone and white floral fragrance in which the mint-like and camphor-like fragrance is weaker resulting in a softer aroma overall, and was found to be useful in formulated perfumes having a white floral scent.

In addition, by using the compounds of the present invention as the starting material, optically active trans-1-(2,2,6-trimethycyclohexyl)-2-buten-1-one ((1S,6R) form (10a), (1R,6S) form (10b)), which is useful as a floral and fruity perfume, can be provided inexpensively according to the production method indicated below.

Reaction scheme C

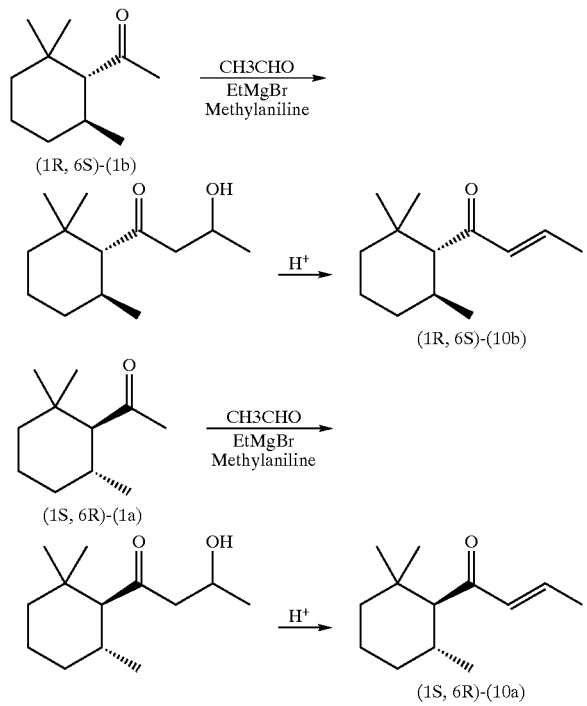

Namely, after allowing trans-(1S,6R)- or (1R,6S)-2,2,6-trimethylcyclohexyl methyl ketone ((1a) or (1b)) to act with an Aldol reagent formed with an alkyl magnesium bromide (or chloride) typified by ethyl magnesium chloride and N-methylaniline (or other dialkylamine), it is reacted with acetaldehyde to synthesize an aldol form. The resulting aldol form is dehydrated using a protonic acid such as PTS (paratoluenesulfonic acid) as a dehydration catalyst to synthesize (1S,6R)- and/or (1R,6S)-1-(2,2,6-trimethylcyclohexyl)-2-buten-1-one ((1S,6R) form (10a), (1R,6S) form (10b)) with high selectivity.

Thus, the trans-(1R,6S)-2,2,6-trimethylcyclohexyl methyl ketone represented by the above-mentioned general formula (1b) and the trans-(1S,6R)-2,2,6-trimethylcyclohexyl methyl ketone represented by the general formula (1a) can be used as a fragrance agent or fragrance improvement enhancer having a characteristic, strongly dispersing, highly tasteful and unique fragrance, thereby making it possible to provide fragrant cosmetics, health and hygiene materials, pharmaceuticals and so forth containing these as fragrant ingredients.

Specifically, product value can be enhanced by blending a suitable amount that is able to provide a unique fragrance to shampoo, body shampoo, rinse, perfume, cologne, hair tonic, hair cream, pomade, other cosmetic bases for hair growers, face powder, lipstick, other cosmetic bases and cosmetic cleaners, soap, liquid soap, dish washing soap, laundry detergent, softener, room air fresheners, furniture polish, bleach, disinfectant, insecticide, repellent, other various types of health an hygiene cleaners, toothpaste, mouthwash, toilet paper and fragrances for facilitating the taking of pharmaceuticals.

In addition, optically active 1-(2,2,6-trimethylcyclohexyl)-2-buten-1-one can be provided inexpensively that is useful as a floral fruity perfume by using the compounds of the present invention in the form of trans-(1R,6S)- and (1S,6R)-2,2,6-trimethylcyclohexyl methyl ketones represented by the general formulas (1b) and (1a) as starting materials.

EXAMPLES

The present invention will be described below in more detail by way of the following Examples, but the present invention is not limited in any way to these examples. It should be noted that the following equipment was used to determine the physical properties of the compounds obtained in the following Examples and Comparative examples.

NMR: DRX500 (Bruker)
GLC: 5890 (Hewlett Packard)
Gc column: Neutrabond-1
GC-MS: HP6890-5973MSD (Hewlett Packard)
(HP-1 MS 60 m×0.25 mm)

Asymmetric yield was measured either by measuring optical rotation or using an optical activity separation column.

Reference Example 1

Synthesis of (4S)-4,8-dimethyl-7-nonen-2-ol: (4S)-(13)

Magnesium (50 g) and tetrahydrofuran (100 ml) were placed in a 2-liter, 4-necked flask equipped with an intake tube (for methyl chloride), thermometer, condenser and stirrer under a nitrogen stream, followed by heating to 40° C. and adding iodine (one piece) and methyl iodide (1 ml) to activate the magnesium. Then, tetrahydrofuran (600 ml) was added and methyl chloride gas was introduced through the intake tube while stirring. The resulting mixture was then allowed to react at 40 to 45° C. until the magnesium powder disappeared (requiring 2 to 3 hours) to prepare a solution of methylmagnesium chloride in tetrahydrofuran.

After completion of the reaction, the solution was cooled to room temperature and (3S)-citronellal (290 g: Takasago International Corporation, optical purity: 98% e.e.) was added dropwise over the course of 3 hours while cooling with ice. After the dropwise addition, the solution was stirred at the same temperature for 2 hours. After the reaction was completed, the solution was cooled and a solution of water (108 g) in tetrahydrofuran (200 ml) was added dropwise to decompose the unreacted methylmagnesium chloride and the thus produced alcolate. The formed magnesium chloride hydroxide as a solid was removed using a filter and the resulting solution of the product in tetrahydrofuran was concentrated with an evaporator to obtain a concentrated oil (316 g). The resulting concentrated oil (316 g) was distilled with a Widmer distiller to obtain 296 g of (4S)-4,8-dimethyl-7-nonen-2-ol ((4S)-(13)) (b.p.: 70–71° C./13.3 Pa (0.1 torr)).

Gas chromatography of the resulting fraction yielded a value of 99.8%, and spectral data indicated the values shown below.

GC/MS (m/e); 170 (M$^+$, 10%), 152 (2), 137 (8), 109 (70), 95 (65), 82 (100), 69 (80), 55 (50), 43 (76)
IR (NaCl); 3343 cm$^{-1}$ (br)
NMR [δ (CDCl$_3$)]; 5.10 (t, 1H, J=7.1 Hz), 3.89 (dq 1H, J=12.8, 6.2 Hz), 2.0 (m, H), 1.68 (s, 3H), 1.60 (s, 3H), 1.55 (m, 1H), 1.5 (m, 1H), 1.4 (m, 2H), 1.19 (d, 3H, J=6.2 Hz), 1.1 (m, 1H), 0.91 (d, 3H, J=6.6 Hz).

Reference Example 2

Synthesis of (4S)-4,8-dimethyl-7-nonen-2-one: (4S)-(14)

Acetone (2,000 ml) and the (4S)-4,8-dimethyl-7-nonen-2-ol (240 g) synthesized in Reference Example 1 were placed in a 5-liter, 4-necked flask equipped with a dropping funnel, thermometer, condenser and stirrer. Jones reagent (prepared from water (520 ml), conc. sulfuric acid (165 g) and chromium trioxide (112 g)) placed in the dropping funnel was dropped in over the course of 4 hours while cooling with ice. After the dropwise addition, the mixture was stirred for 2 hours. The sodium hydrogen sulfite was added little by little until the orange color of chromium (VI) disappeared. The liquid was then separated and the bottom layer was extracted with petroleum ether (1,000 ml). Since the liquid was again separated into two layers when the extract was combined with the top layer, that bottom layer was added to the previous bottom layer and additionally extracted three times with 500 ml of petroleum ether. After combining the extracts and washing with a saturated brine, a saturated aqueous sodium hydrogencarbonate solution and again with a saturated brine, the solvent was distilled off and the resulting concentrated oil was distilled with a Widmer distiller to obtain 194 g of (4S)-4,8-dimethyl-7-nonen-2-one: (4S)-(14) (b.p.: 63° C./133 Pa (1.0 torr)).

Gas chromatography of the resulting fraction yielded a value of 99.5%, and spectral data indicated the values shown below.

GC/MS (m/e); 168 ($M^+$, 19%), 150 (8), 135 (25), 110 (58), 95 (100), 85 (42), 69 (47), 43 (64)

IR (NaCl); 1716 $cm^{-1}$

NMR [δ ($CDCl_3$)]; 5.09 (t, 1H, J=7.1 Hz), 2.42 (dd, 1H, J=5.6, 15.7 Hz), 2.22 (dd, 1H, J=8.2, 15.7 Hz), 2.0 (m, 1×3H), 1.68 (s, 3H), 1.3 (m, 1H), 1.2 (m, 1H), 0.91 (d, 3H, J=6.6 Hz).

Reference Example 3

Synthesis of (4S)-4,8-dimethyl-2,7-(and -1,7-)-nonadien-2-yl Acetate: (4S)-(2)

The (4S)-4,8-dimethyl-7-nonen-2-one (168 g) synthesized in Reference Example 2, isopropenyl acetate (200 g) and paratoluenesulfonic acid·monohydrate (19 g) were placed in a 3,000 ml, 4-necked flask equipped with a thermometer, condenser and stirrer under a nitrogen stream, followed by reacting at 90° C. for 22 hours while stirring. As a result of sampling the product and analyzing by gas chromatography, it was confirmed by the mass spectral data shown below that three types of (4S)-4,8-dimethyl-2,7-(and 1,7)-nonadien-2-yl acetate: (4S)-(2) (composition: 50.3%, 16.4%, 26.8%) were formed. The products were then subjected to a cyclization reaction without treating.

Mass spectra of three types of (4S)-4,8-dimethyl-2,7-(and 1,7)-nonadien-2-yl acetate:

(4S)-[2-1]; 210 ($M^+$, 1%), 168 (17), 150 (68), 135 (38), 109 (77), 95 (57), 85 (100), 69 (47), 43 (100)

(4S)-[2-2]; 210 ($M^+$, 1%), 168 (10), 150 (57), 135 (30), 109 (68), 95 (43), 85 (98), 69 (36), 43 (100)

(4S)-[2-3]; 210 ($M^+$, 1%), 167 (8), 150 (64), 135 (38), 109 (100), 95 (75), 85 (30), 69 (62), 43 (94)

IR and NMR spectra of a mixture of three types of (4S)-4,8-dimethyl-2,7-(and 1,7)-nonadien-2-yl acetate:

IR (NaCl); 1756 $cm^{-1}$, 1213 $cm^{-1}$

NMR [δ ($CDCl_3$)]; 5.06 (t, 1H), 4.74 (t, 1H, 10.6 Hz), 2.11 (s, 3H), 2.0 (m, 2H), 1.66 (s, 3H), 1.58 (s, 3H), 1.1 (m, 2H), 1.0 (m, 1H), 0.91 (d, 3H).

Example 1

Synthesis of (1R,6S)-2,2,6-trimethylcyclohexyl methyl ketone (1b)

85% phosphoric acid (50 g) and toluene (1,500 ml) were added to a reaction liquid containing a mixture of the three types of (4S)-4,8-dimethyl-2,7-(and 1,7)-nonadien-2-yl acetate synthesized in Reference Example 3 and the resulting mixture was reacted at 100° C. for 32 hours. After cooling the reaction liquid, and washing with water, a saturated aqueous sodium carbonate solution and a saturated brine, the solvent was distilled off and the resulting concentrated oil (purity as determined by gas chromatography: (1R,6S)-(1): 64.5%, (1S,6S)-(1): 1.1% and small amounts of other unknown components: 34.4%) was purified with a 50-stage precision distiller to obtain 71 g of (1R,6S)-2,2,6-trimethylcyclohexyl methyl ketone (b.p.: 78° C./1197 Pa (9 torr)).

Gas chromatography of the resulting fraction yielded a value of 98.6%, exhibited optical rotation of $[\alpha]_D$=−23.80° (c 1.00, EtOH, 24° C.), and demonstrated spectral data having the values shown below.

GC/MS (m/e); 168 ($M^+$, 34%), 153 (10), 135 (17), 125 (20), 110 (62), 99 (100), 85 (45), 69 (89), 43 (62)

IR (NaCl); 1708 $cm^{-1}$

NMR [δ ($CDCl_3$)]; 2.16 (s, 3H), 2.07 (d, 1H, J=11.2 Hz), 1.8 (m, 1H), 1.7 (dq, 1H), 1.5 (m, 2H), 1.4 (ddd, 1H, J=1.4, 3.3, 13.1), 1.2 (m, 1H), 0.96 (s, 3H), 0.93 (s, 3H), 0.9 (m, 1H), 0.81 (d, 3H, J=6.3 Hz).

Example 2

Synthesis of Trans-(1S,6R)-2,2,6-trimethylcyclohexyl methyl ketone (1a)

Reaction was carried out in exactly the same manner of synthesis for formulations as Reference Examples 1 through 3 and Example 1 using for the starting material (3R)-citronellal (Takasago International Corporation, optical purity: 98% e.e.) to obtain 73 g of trans-(1S,6R)-2,2,6-trimethylcyclohexyl methyl ketone (1a) (b.p.: 78° C./1197 Pa (9 torr), $[\alpha]_D$=+23.98° (c 1.00, EtOH, 24° C.), purity as determined by gas chromatography: 98.8%).

Reference Example 4

Synthesis of (1R,6S)-1-(2,2,6-trimethylcyclohexyl)-ethan-1-ol (15b)

Magnesium (50 g) and tetrahydrofuran (100 ml) were placed in a 2-liter, 4-necked flask equipped with an intake tube (for methyl chloride), thermometer, condenser and stirrer under a nitrogen stream, followed by heating to 40° C. and adding iodine (one piece) and methyl iodide (1 ml) to activate the magnesium. Then, tetrahydrofuran (600 ml) was added to the mixture and methyl chloride gas was introduced through the intake tube while stirring. These were then allowed to react at 40 to 45° C. until the magnesium powder disappeared (requiring 2 to 3 hours) to prepare a solution of methyl magnesium chloride in tetrahydrofuran.

After completion of the reaction, the solution was cooled to room temperature and (1R,6S)-2,2,6-trimethylcyclohexyl carbaldehyde (11) (290 g, produced in accordance with the method of JP-2748184 using as starting material the 7-methoxycitronellal having an optical purity of 98% e.e. of Takasago International Corporation, composition as determined by gas chromatography: (1R,6S) (11): 92.9%, (1S, 6S)-(11): 7.1%) was added dropwise over the course of 3 hours while cooling with ice. After dropwise addition, the solution was stirred at the same temperature for 2 hours to complete the reaction. Then, the solution was cooled and a solution of water (108 g) in tetrahydrofuran (200 ml) was added dropwise to decompose the unreacted methyl magnesium chloride and the thus produced alcolate. The thus formed magnesium chloride hydroxide in the form of a solid was removed using a filter and the resulting solution of the product in tetrahydrofuran was concentrated with an evaporator to obtain a concentrated oil (316 g). The resulting concentrated oil (316 g) was distilled with a Widmer distiller to obtain 293 g of (1R,6S)-1-(2,2,6-trimethylcyclohexyl)-ethan-1-ol (15b) (b.p.: 60° C./33.25 Pa (0.25 torr)).

The spectral data indicated the values shown below.
GC/MS (m/e); 170 (M$^+$, 0%), 152 (1), 137 (10), 125 (45), 111 (92), 95 (19), 83 (70), 69 (100), 55 (60), 41 (49)

IR (NaCl); 3442 cm$^{-1}$ (br)

NMR [δ (CDCl$_3$)]; 4.14 (q, 1H, J=6.9 Hz), 1.7 (m, 1H), 1.4 (m, 2H), 1.3 (m, 1H), 1.30 (d, 3H, 6.9 Hz), 1.2 (m, 1H), 1.15 (d, 3H, J=7.3 Hz), 1.1 (m, 1H), 1.0 (m, 1H), 0.91 (s, 3H), 0.90 (s, 3H), 0.81 (d, 1H, J=10.9 Hz).

Reference Example 5

Synthesis of (1R,6S)-2,2,6-trimethylcyclohexyl methyl ketone (1b)

The (1R,6S)-1-(2,2,6-trimethylcyclohexyl)-ethan-1-ol (15b) (250 g) synthesized in Reference Example 4 and a copper-chromium catalyst (12.5 g) pre-activated with hydrogen were placed in a 500 ml, 4-necked flask equipped with a thermometer, condenser and stirrer, followed by reacting at 200° C. for 6 hours. After cooling the reaction mixture and filtering out the catalyst, the reaction liquid was distilled with a Widmer distiller to obtain 224 g of (1R,6S)-2,2,6-trimethylcyclohexyl methyl ketone (1b) (b.p.: 76–78° C./1197 Pa (9 torr)).

The composition of the resulting fraction as determined by gas chromatography was 93.9% of the (1R,6S) form (1b), and 6.1% of the (1S,6S) form (1d).

Reference Example 6

Synthesis of (1R,6S)-1-(2,2,6-trimethylcyclohexyl)-2-buten-1-one (10b)

A solution containing N-methylaniline (23.8 g) dissolved in 70 ml of toluene was added while ice-cooling and stirring to a tetrahydrofuran solution (82 ml) of ethyl magnesium bromide, produced in 60 ml of tetrahydrofuran from ethyl bromide (30.0 g) and magnesium (5.9 g), in a 500 ml, 4-necked flask equipped with a thermometer, condenser and stirrer under a nitrogen stream. While maintaining this freshly prepared N-methylaniline-magnesium bromide solution at a temperature of 10 to 15° C., a solution of the (1R,6S)-2,2,6-trimethylcyclohexyl methyl ketone (1b) (37 g) synthesized in Example 1 in toluene (37 ml) was added dropwise over the course of 30 minutes, followed by additionally stirring at the same temperature for 30 minutes.

Next, a solution of acetaldehyde (14.6 g) in toluene (15 ml) was added dropwise over a course of 30 minutes at 0° C. and additionally stirred for 90 minutes following completion of dropping. 3 N hydrochloric acid (150 ml) was then added to the reaction liquid while stirring and cooling with ice to conduct decomposition, washing with water, and separation, after which the organic layer was washed five times with 100 ml of 3 N hydrochloric acid each time and separated. After adding paratoluenesulfonic acid (0.5 g) to a toluene solution of the resulting aldol form (4-(2,6,6-trimethyl-2-cyclohexyl)-4-oxo-butan-2-ol) and heating, the water formed due to the dehydration reaction was separated under reflux with toluene to complete the dehydration reaction. After adding 50 ml of water to the reaction liquid and washing until separation, the liquid was washed and separated with 50 ml of aqueous sodium bicarbonate solution and 50 ml of water, after which the resulting organic layer was washed with an evaporator to obtain 45 g of concentrated oil. This was then distilled with a Widmer distiller to obtain 28 g of (1R,6S)-1-(2,2,6-trimethylcyclohexyl)-2-buten-1-one (10b) (b.p.: 73–75° C./19.95 Pa (0.15 torr), [α]$_D$=−16.10° (c 1.00, EtOH, 24° C.))

The composition of this fraction as determined by gas chromatography demonstrated the isomeric composition values shown in Table 2 below, and had superior fragrance characteristics.

TABLE 2

| Isomer | t-(1R, 6S)-(10) | cis-(1R, 6S)-(10) | t-(1S, 6S)-(10) | cis-(1S, 6S)-(10) |
|---|---|---|---|---|
| Composition | 92.9% | 5.8% | 1.3% | 0.1% |

Reference Example 7

Synthesis of (1S,6R)-1-(2,2,6-trimethyl-1-cyclohexyl)-2-buten-1-one (10a)

The reaction was carried out in exactly the same manner as Reference Example 6 using 37 g of the (1S,6R)-2,2,6-trimethylcyclohexyl methyl ketone (1a) synthesized in Example 2 to obtain 29 g of (1S,6R)-1-(2,2,6-trimethylcyclohexyl)-2-buten-1-one (10a) (b.p.: 73–75° C./19.95 Pa (0.15 torr), [α]$_D$=+15.52° (c 1.00, EtOH, 24° C.).

The composition of this fraction as determined by gas chromatography demonstrated the isomeric composition values shown in Table 3 below, and had superior fragrance characteristics.

TABLE 3

| Isomer | 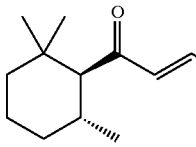 | 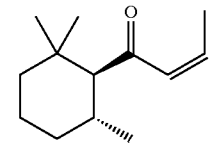 | 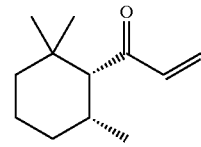 | 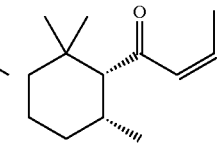 |
|---|---|---|---|---|
| | t-(1S, 6R)-(10) | cis-(1S, 6R)-(10) | t-(1R, 6R)-(10) | cis-(1R, 6R)-(10) |
| Composition | 93.1% | 5.9% | 1.0% | 0.1% |

Formulation Examples 1 to 5

A men's cologne base of the formulation indicated below having a fougere note was prepared.

| Fragrance name | Formulated amount (parts by weight) |
|---|---|
| Allyl amylglycolate | 6 |
| Amyl salicylate | 60 |
| 4-(2,2,3-Trimethyl-3-cyclopenten-1-yl)-2-ethyl-2-buten-1-ol | 7 |
| Benzyl salicylate | 100 |
| Cedryl acetate | 10 |
| Cinnamic alcohol | 5 |
| Coumarin | 5 |
| Dihydromyrcenol | 180 |
| Dipropylene glycol | 150 |
| Eugenol | 10 |
| Geranyl acetate | 2 |
| Lavandin | 15 |
| Citral | 5 |
| Lemon oil California | 20 |
| p-t-Butyldihydrocinnamic aldehyde | 12 |
| Linalool | 17 |
| Linalyl acetate | 70 |
| Neryl acetate | 2 |
| Orange oil | 100 |
| Terpineol | 7 |
| Terpinyl acetate | 5 |
| Tetrahydrolinalool | 70 |
| Triplal (produced by IFF) | 2 |
| Cedar wood oil | 35 |
| Ylang FT-9237B | 10 |
| Patchouli oil | 25 |
| Total (parts by weight) | 930 |

A fragrance having a fougere note (Formulation 1) with high tasteful appeal as a men's cologne was prepared using 930 parts by weight of the above fougere base and 70 parts by weight of (1a) of 98% e.e. synthesized in Example 1. Fougere fragrances (Formulations 2 to 5) were also produced using 70 parts by weight each of optical purity of (1a) and racemic form (mixtures of equal amount of 1a and 1b) obtained by mixing prescribed amounts of (1b) of 98% e.e. similarly synthesized in Example 2 with the above (1a). Those compositions are shown in Table 4.

| Formulated product name | Formulation 1 | Formulation 2 | Formulation 3 | Formulation 4 | Formulation 5 |
|---|---|---|---|---|---|
| Fougere base described above | 930 | 930 | 930 | 930 | 930 |
| 98% e.e. (1a) | 70 | 0 | 0 | 0 | 0 |
| 85% e.e. (1a) | 0 | 70 | 0 | 0 | 0 |
| 75% e.e. (1a) | 0 | 0 | 70 | 0 | 0 |
| 65% e.e. (1a) | 0 | 0 | 0 | 70 | 0 |
| Racemic form (equal amounts of 1a and 1b) | 0 | 0 | 0 | 0 | 70 |
| Total (parts by weight) | 1000 | 1000 | 1000 | 1000 | 1000 |

Which of the fragrances of formulations 2 through 5 exhibited high appeal as a result of having a fragrance similiar to formulation 1 was assessed by 30 panelists by comparing with formulation 1 having highly taste-appealing fragrance. As a result, 8 of the panelists preferred formulation 2 (85% e.e.) as having a similar fragrance to formulation 1, while formulations 4 and 5 were indicated as being quite different. In addition, 19 panelists responded that they preferred formulation 3 (75% e.e.) because it somewhat resembled the fragrance of formulation 1, but they did not prefer formulas 4 and 5 due to a poor top note balance. In addition, 3 panelists responded that they also liked formulation 4 but did not like formulation 5.

Formulation Example 6

The eucalyptus oil (17 parts by weight) component of the vegetable green-scented shampoo fragrance having the formula shown below was replaced with 98% e.e. (1a) (17 parts by weight) synthesized in Example 1 to produce a vegetable green-scented shampoo fragrance that had higher taste-appeal than the original.

| Name of fragrance used | Formulated amount (parts by weight) |
|---|---|
| Eucalyptus oil | 17 |
| Allyl amylglycolate | 5 |
| Benzyl acetate | 80 |
| Benzyl benzoate | 5 |
| L-citronellol | 15 |
| L-citronelyl acetate | 5 |

-continued

| Name of fragrance used | Formulated amount (parts by weight) |
|---|---|
| Cyclamen aldehyde | 7 |
| Dihydromyrcenol | 9 |
| Dihydromyrcenyl formate | 5 |
| Dimethyloctanol | 2 |
| Dipropylene glycol | 60 |
| Geraniol | 45 |
| Geranyl acetate | 15 |
| Methyl dihydrojasmonate | 70 |
| Heliotropine | 5 |
| Cis-3-hexenol | 10 |
| Cis-3-hexenyl acetate | 10 |
| Hexylcinnamic aldehyde | 50 |
| Indole | 1 |
| Cisjasmone | 1 |
| L-rose oxide | 1 |
| Citral | 2 |
| Linalool | 150 |
| Linalyl acetate | 40 |
| Nerol | 20 |
| Nerolidol | 5 |
| Neryl acetate | 5 |
| Orange terpen import | 62 |
| Phenylacetaldehyde dimethylacetal | 3 |
| Phenylethyl acetate | 8 |
| Phenylethyl alcohol | 15 |
| Styrallyl acetate | 6 |
| Terpineol | 51 |
| Triplal (produced by IFF) | 15 |
| Total | 1000 |

Formulation Example 7

The highly taste-appealing white floral-scented fragrance having the formulation indicated below was produced using 98% e.e. (1b) synthesized in Example 2.

| Name of fragrance used | Formulated amount (parts by weight) |
|---|---|
| 98% e.e. (1b) | 15 |
| Aldehyde C9 | 1 |
| Benzyl salicylate | 40 |
| L-citronellol | 100 |
| L-citronelyl acetate | 10 |
| Cyclamen aldehyde | 10 |
| p-Isobutyldihydrocinnamic aldehyde | 3 |
| Methyl dihydrojasmonate | 140 |
| Cis-3-hexenyl acetate | 1 |
| Hexylcinnamic aldehyde | 100 |
| Indole | 2 |
| 4-(4-hydroxy-4-methylpentyl)-cyclohexylcarbaldehyde | 200 |
| L-laurinal | 35 |
| p-t-Butyldihydrocinnamic aldehyde | 100 |
| Linalool | 50 |
| Hexyl benzoate | 15 |
| Phenylethyl acetate | 10 |
| Phenylethyl alcohol | 50 |
| Phenylethyl salicylate | 25 |
| Rose oxide | 2 |
| Isocamphyr cyclohexanol | 60 |
| Triplal (produced by IFF) | 1 |
| Benzyl propionate | 30 |
| Total | 1000 |

It should be apparent to those skilled in the art that the present invention may be embodied in many other specific forms without departing from the spirit or scope of the invention.

Therefore, the present examples and embodiments are to be considered as illustrative and not restrictive and the invention is not to be limited to the details given herein, but may be modified within the scope and equivalence of the appended claims.

What is claimed is:

1. A composition comprising:

at least one of a (1S,6R)-2,2,6-trimethylcyclohexyl methyl ketone represented by the formula (1a):

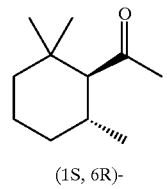

(1a)

(1S, 6R)- and at least one of a (1R,6S)-2,2,6-trimethylcyclohexyl methyl ketone represented by the formula (1b):

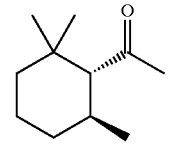

(1b)

(1R, 6S)- wherein the optical purity of the 2,2,6-trimethylcyclohexyl methyl ketone in the composition is at least 75% e.e.

2. The composition according to claim 1, wherein the optical purity of the 2,2,6-trimethylcyclohexyl methyl ketone in the composition is from 75% e.e. to 98% e.e.

3. A perfume composition comprising:

at leat one of a (1S,6R)-2,2,6-trimethylcyclohexyl methyl ketone represented by the formula (1a):

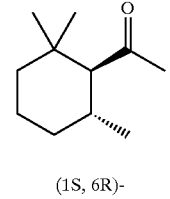

(1a)

(1S, 6R)- and at least one of a (1R,6S)-2,2,6-trimethylcyclohexyl methyl ketone represented by the formula (1b):

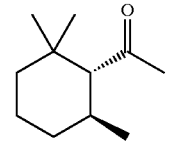

(1b)

(1R, 6S)- and an acceptable carrier
wherein the optical purity of the 2,2,6-trimethylcyclohexyl methyl ketone in the composition is at least 75% e.e.

4. The perfume composition according to claim 3, wherein the optical purity of 2,2,6-trimethylcyclohexyl methyl ketone in the composition is from 75% e.e. to 98% e.e.

5. A process for producing trans-2,2,6-trimethylcyclohexyl methyl ketone, comprising at least one of a compound represented by the formula (1a):

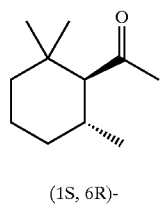

(1S, 6R)- and a compound represented by the formula (1b):

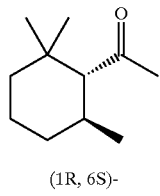

(1R, 6S)- the process comprising:
cyclizing a novel optically active enol acetate represented by at least one of formula (2a):

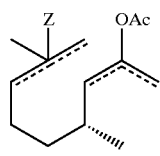

(4R)-(2)

and formula (2b):

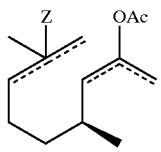

(4S)-(2)

wherein Ac represents an acetyl group; double lines composed of solid lines and broken lines represent a double bond or single bond; when said double lines represent a single bond, Z represents a hydroxyl group or a methoxy group; and, when said double lines represent a double bond, Z is absent, in the presence of an acid catalyst.

6. The process for producing trans-2 2 6-trimethylcyclohexyl methyl ketone according to claim 5, where said acid catalyst is a protonic acid.

7. The process for producing trans-2,2,6-trimethylcyclohexyl methyl ketone according to claim 6, wherein said protonic acid is selected from the group consisting of hydrochloric acid, sulfuric acid, phosphoric acid, polyphosphoric acid, para-toluenesulfonic acid, napthalene sulfonic acid, a sulfonated styrene-divinylbenzene polymer, sulfuric acid-carrying activated clay and a perfluorosulfonic acid polymer.

8. The process for producing trans-2,2,6-trimethylcyclohexly methyl ketone according to claim 5, wherein said acid catalyst is present from about 0.1 to 5 equivalents relative to 1 equivalent of the enol acetate.

\* \* \* \* \*